US007485626B2

(12) United States Patent
Ansorge et al.

(10) Patent No.: US 7,485,626 B2
(45) Date of Patent: Feb. 3, 2009

(54) COMBINATIONS OF ENZYME INHIBITOR-CONTAINING PREPARATIONS AND THE USE THEREOF

(75) Inventors: Siegfried Ansorge, Hohenwarthe (DE); Marco Arndt, Merseburg (DE); Frank Buehling, Magdenburg (DE); Uwe Lendeckel, Magdeburg (DE); Klaus Neubert, Halle/Saale (DE); Dirk Reinhold, Magdeburg (DE); Stefan Brocke, Berlin (DE)

(73) Assignee: IMTM GmbH, Magdeburg (DE)

( * ) Notice: Subject to any disclaimer, the term of this patent is extended or adjusted under 35 U.S.C. 154(b) by 92 days.

(21) Appl. No.: 10/296,102

(22) PCT Filed: May 22, 2001

(86) PCT No.: PCT/EP01/05887

§ 371 (c)(1),
(2), (4) Date: Mar. 26, 2004

(87) PCT Pub. No.: WO01/89569

PCT Pub. Date: Nov. 29, 2001

(65) Prior Publication Data

US 2005/0014699 A1    Jan. 20, 2005

(30) Foreign Application Priority Data

May 23, 2000   (DE)   ............................... 100 25 464

(51) Int. Cl.
*A61K 38/00*   (2006.01)
*A61K 31/69*   (2006.01)
*A61K 31/675*  (2006.01)
*A61K 31/445*  (2006.01)
*A01N 55/08*   (2006.01)
*A01N 43/40*   (2006.01)
*A01N 43/36*   (2006.01)

(52) U.S. Cl. ............................. 514/19; 514/64; 514/79; 514/317; 514/423

(58) Field of Classification Search ........................ None
See application file for complete search history.

(56) References Cited

U.S. PATENT DOCUMENTS

2004/0132639 A1 *  7/2004  Ansorge et al. ................. 514/7
2004/0147434 A1 *  7/2004  Ansorge et al. ............... 514/12
2005/0014699 A1 *  1/2005  Ansorge et al. ............... 514/19

FOREIGN PATENT DOCUMENTS

WO    WO 98/44923    * 10/1998
WO    WO 99/46272    *  9/1999

OTHER PUBLICATIONS

Augustijns et al. Transport and Metabolism of Delta Sleep-Inducing Peptide in Cultured Human Intestinal Epithelial Cell Monolayers. Durg Metabolism and Disposition. 1995, vol. 23 No. 1. pp. 1372-1378.*
http://www.thelabrat.com/protocols/Hanks.shtml, accessed online Jan. 31, 2007 (2 pages).*
http://www.cellgro.com/shop/files/documents/HEPES_Buffer.pdf, accessed online Jan. 31, 2007 (1 page).*
http://www.answers.com/neoplasia&r=67 accessed online Feb. 1, 2007 (1 page).*
Steinmetzer, et al., Peptidyl Ammonium Methyl Ketones As Substrate Analog Inhibitors of Proline-Specific Peptidases, J. Enzyme Inhibition, 1993, vol. 7, pp. 77-85.
Ansorge, et al., Membrane-bound peptidases of lymphocytes: Functional implications, Biomed. Biochim. Acta 50 (1991) 4-6, pp. 799-807.
Shimazawa, et al., Novel Small Molecule Nonpeptide Aminopeptidease N Inhibitors With A Cyclic Imide Skeleton, J. Enzyme Inhibition, 1999, vol. 14, pp. 259-275.
Augustyns, et al., The Unique Properties of Dipeptidyl-peptidase IV (DPP IV / CD 26) and the Therapeutic Potential of DPP IV Inhibitors, Current Medicinal Chemistry, 1999, 6, pp. 311-227.
Reinhold, et al., Inhibitors of dipeptidyl peptidase IV induce secretion of transforming growth factor-$\beta_1$ in PWM-stimulated PBMC and T cells, 1997 Blackwell Science Ltd, Immunology 1997 91, pp. 354-369.
Hendriks, et al.; Aminopeptidase P and Dipeptidyl Peptidase IV Activity In Human Leukocytes And In Stimulated Lymphocytes; Clinica Chimica Acta, vol. 196 (1991) pp. 87-96.
Kitamura, et al.; Effects Of Aminopeptidase P Inhibition On Kinin-Mediated Vasodepressor Responses; Am. J. Physiol Heart Circ Physiol, vol. 276, 1999; pp. 1664-1671.
Clozel, et al.; Endothelial Dysfunction And Subendothelial Monocyte Macrophages In Hypertension Effect Of Angiotensin Converting Enzyme Inhibition; Hypertension, 1991, vol. 18, No. 2; pp. 132-141.

* cited by examiner

*Primary Examiner*—Cecilia J Tsang
*Assistant Examiner*—Marcela M Cordero Garcia
(74) *Attorney, Agent, or Firm*—Hodgson Russ LLP

(57) ABSTRACT

The invention comprises a process wherein the DNA synthesis and, thus, the proliferation of mononuclear cells (MNZ) and of T cells as well is inhibited by the simultaneous and combined inhibition of the enzyme activity (I) of alanyl aminopeptidase and of dipeptidyl peptidase IV; (II) of dipeptidyl peptidase IV and of the angiotensin-converting enzyme; (III) of dipeptidyl peptidase IV and of prolyl oligopeptidase; and (IV) of dipeptidyl peptidase IV and of X-Pro-aminopeptidase to an extent which cannot be achieved by an application of a single one of said enzyme inhibitors, even at a higher dosage. Although the said inhibitors exercise an influence on the very same process finally, i.e. the DNA synthesis and, thus, the proliferation of immune cells, this effect is not complete and is not long lasting when a single inhibitor is applied. From the functional overlap of enzymatic activities results an additive/superadditive inhibitory effect on the DNA synthesis and proliferation by the simultaneous inhibition of more than one of the above enzymes, as our data show.

Figure 1:
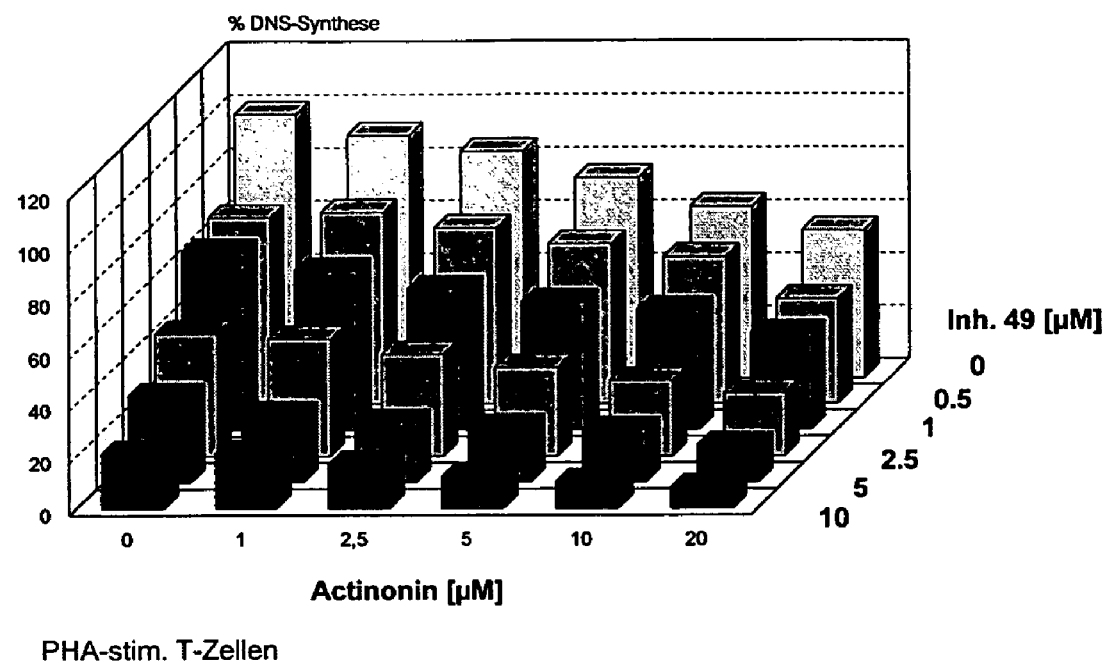

Our invention shows that the simultaneous application of substances inhibiting the above enzymes or of corresponding preparations and administration forms, respectively, is well suitable for a therapy of autoimmune diseases and chronic diseases with an inflammatory genesis as well as for a treatment of rejection episodes after a transplantation.

7 Claims, 8 Drawing Sheets

PHA-stim. T-Zellen

PHA-stim. MNZ

PHA-stim. T-Zellen

PHA-stim. MNZ

PHA-stim. T-Zellen

PHA-stim. MNZ-Zellen

COMBINATIONS OF ENZYME INHIBITOR-CONTAINING PREPARATIONS AND THE USE THEREOF

The present invention describes the combined inhibition of the activity of the enzymes Aminopeptidase N (APN; E.C. 3.4.11.2.; CD13), Dipeptidyl peptidase IV (DP IV; E.C. 3.4.14.5; CD26), Prolyl oligopeptidase (POP; Prolyl endopeptidase; PEP; E.C. 3.4.21.26), the membrane-adherent Aminopeptidase P (X-Pro-Aminopeptidase; APP; XPN-PEP2; E.C. 3.4.11.9) and Angiotensin-converting Enzyme (Angiotensin-konvertierendes Enzym; ACE; CD156; E.C. 3.4.15.1; CD156) by a simultaneous application of respective specific inhibitors of the above-referenced enzymes on the basis of amino acid derivatives, peptides or peptide derivatives, by which the activation, the DNA synthesis and, thus, the proliferation of immune cells is suppressed.

It is applicable to all diseases showing autoimmune pathogenesis that the disease is based on, or consists of, an activation and proliferation of immune cells, in particular of autoreactive T cells. The very same mechanisms effect the acute or chronic rejection episodes after a transplantation of organs.

It was shown that membrane-adherent peptidases as, for example, DP IV or APN play a key role in the process of activation and clonal expansion of immune cells, particularly of T lymphocytes [B. Fleischer: "CD26, a surface protease involved in T cell activation", Immunology Today 1994, 15, 180-184; U. Lendeckel et al.: "Role of alanyl peptidase in growth and function of human T cells", International Journal of Molecular Medicine 1999, 4, 17-27; D. Riemann et al.: "CD13—not just a marker in leukemia typing", Immunology Today 1999, 20, 83-88]. Several functions of mitogene-stimulated mononuclear cells (mitogen-stimulierte mononukleäre Zellen; MNZ) or of enriched T lymphocytes as, for example, the DNA synthesis, production and secretion of immune-stimulating cytokines (IL-2, IL-6, IL-12, IFN-γ) and helper functions for B cells (synthesis of IgG and IgM) may be inhibited in the presence of specific inhibitors DP IV and APN [E. Schön et al.: "The dipeptidyl peptidase IV, a membrane enzyme involved in the proliferation of T lymphocytes", Biomed. Biochim Acta 1985, 2, K9-K15; E. Schön et al.: "The role of dipeptidyl peptidase IV in humane T lymphocyte activation, inhibitors and antibodies against dipeptidyl peptidase IV suppress lymphocyte proliferation and immunoglobulin synthesis in vitro", Eur. J. Immunol. 1987, 17, 1821-1826; D. Reinhold et al.: "Inhibitors of dipeptidyl peptidase IV induce secretion of transforming growth factor β1 in PWM-stimulated PBMNC and T cells", Immunology 1997, 91, 354-360; U. Lendeckel et al.: "Induction of the membrane alanyl peptidase gene and surface expression in human T cells by mitogenic activation", Biochem. J. 1996, 319, 817-823; T. Kähne et al.: "Dipeptidyl peptidase IV: A cell surface peptidase involved in regulating T cell growth (Review)", Int. J. Mol. Med. 1999, 4, 3-15; U. Lendeckel et al.: "Role of alanyl aminopeptidase in growth and function of human T cells (Review)", Int. J. Mol. Med. 1999, 4, 17-27].

It is already known that the treatment of autoimmune diseases and rejection reactions after transplantations can be effected by an inhibition of dipeptidyl peptidase IV localized on immune cells by means of synthetic inhibitors. Reference is made, for example, to EP 764 151 A1, WO 09529691, EP 731 789 A1, EP 528 858). With respect to the enzymes aminopeptidase N, angiotensin-converting enzyme, X-Pro-aminopeptidase and prolyl oligopeptidase, such effects are not known up to now.

The invention is based on the surprising finding that the simultaneous inhibition of the enzymatic activities of (I) dipeptidyl peptidase IV and aminopeptidase N, (II) dipeptidyl peptidase IV and angiotensin-converting enzyme, (III) dipeptidyl peptidase IV and prolyl oligopeptidase, as well as (IV) dipeptidyl peptidase IV and X-Pro-aminopeptidase inhibits the DNA synthesis and, thus, the proliferation of mononuclear cells (MNZ), and of T cells as well, to an extent which cannot be achieved by the application of a single one of these enzyme inhibitors, even at a higher dosage. Although the above-mentioned inhibitors finally exhibit an effect to the same process, i.e. the DNA synthesis and, thus, the proliferation of immune cells, said effect is marked to a weaker extent and is not long lasting in the case of an application of single inhibitors. Due to the functional overlap of the enzymatic activities of said enzymes, there can be observed a superadditive inhibitory effect on the DNA synthesis and proliferation resulting from the simultaneous inhibition of two or more of these enzymes, as can be concluded from our data.

Our invention shows that the simultaneous application of inhibitory substances of the above-mentioned enzymes or, respectively, of corresponding preparations and administration forms is well suitable for the therapy of autoimmune diseases and inflammatory diseases as well as for the treatment of rejection reactions after a transplantation.

In detail, the invention is based on the finding that the DNA synthesis of mononuclear cells (MNZ) and T cells is inhibited, in a superadditive way, by the simultaneous administration of inhibitors of the enzymatic activities of
(I) dipeptidyl peptidase IV and aminopeptidase N,
(II) dipeptidyl peptidase IV and angiotensin-converting enzyme,
(III) dipeptidyl peptidase IV and prolyl oligopeptidase,
(IV) dipeptidyl peptidase IV and X-Pro-aminopeptidase.

The application of enzyme inhibitors is a new method and complementary therapy form for the treatment of the above-mentioned diseases.

The inhibitors of dipeptidyl peptidase IV, of aminopeptidase N, of prolyl oligopeptidase, of the angiotensin-converting enzyme and of X-Pro-aminopeptidase applied in accordance with the invention may be employed in pharmaceutically applicable formulation complexes as inhibitors, substrates, pseudo-substrates, peptides and peptide derivatives having inhibitory effect and as antibodies of said enzymes as well. Preferred effectors for DP IV are, for example, Xaa-Pro-dipeptides, their corresponding derivatives, preferably dipeptide phosphonic acid diaryl esters and their salts, Xaa-Xaa-(Trp)-Pro-(Xaa)$_n$-peptides (n=0-10), their corresponding derivatives and their salts and amino acid (Xaa)-amides, their corresponding derivatives and salts, wherein Xaa is an α-amino acid/imino acid or an α-amino acid/imino acid derivative, respectively, preferably $N^\epsilon$-4-nitrobenzylcarbonyl-L-lysin, -L-prolin, -L-tryptophan, -L-isoleucin, -L-valin, and cyclic amines as, for example, pyrrolidine, piperidine, thiazolidine, and their derivatives serve as the amide structure. Such compounds and their preparation were described in a prior patent (K. Neubert et al., DD 296 075 A5).

The inhibitors are administered simultaneously with known carrier substances. The administration is conducted, on one hand, as a topical application in the form of, for example, creams, ointments, pastes, gels, solutions, sprays, liposomes, shaked mixtures, hydrocolloid dressings, and other dermatological bases/vehicles, respectively, including instillative applications and, on the other hand, systemic applications for an oral, transdermal, intravenous, subcutaneous, intracutaneous, intramuscular administration in suitable recipes and in a suitable galenic application form, respectively.

WORKING EXAMPLES

Example 1

Inhibition of the DNA Synthesis of Human T Lymphocytes by Incubation with Synthetic Inhibitors of DP IV and of APN

Our investigations showed that the DNA synthesis of human peripheric T lymphocytes is inhibited in a superadditive manner by the simultaneous administration of inhibitors of DP IV (Lys[Z(NO$_2$)]-thiazolidid=I49) and of APN (Actinonin). The T cells were incubated for 72 h in the presence of said inhibitors and subsequently, the DNA synthesis rate was determined via a measurement of the $^3$[H]-thymidin incorporation, as was described by Reinhold et al. [D. Reinhold et al.: "Inhibitors of dipeptidyl peptidase IV induce secretion of transforming growth factor β1 in PWM-stimulated PBMNC and T cells", Immunology 1997, 91, 354-360]. FIG. 1 shows the dose-dependent superadditive inhibition of the DNA synthesis.

FIG. 1 shows the synergistic and dose-dependent effect of inhibitors of DP IV (I49) and aminopeptidase N (actinonine) on the DNA synthesis of human T lymphocytes. Human peripheric T cells were incubated over 3 days with the concentrations of the inhibitors shown. Subsequently, $^3$[H]-methyl thymidine was added to the culture medium, and the amount of $^3$[H]-thymidine inserted into the DNA was measured after further 6 hours.

Example 2

Inhibition of the DNA Synthesis of Human Peripheric Mononuclear Cells by an Incubation with Synthetic Inhibitors of DP IV and of APN

Figure 2:
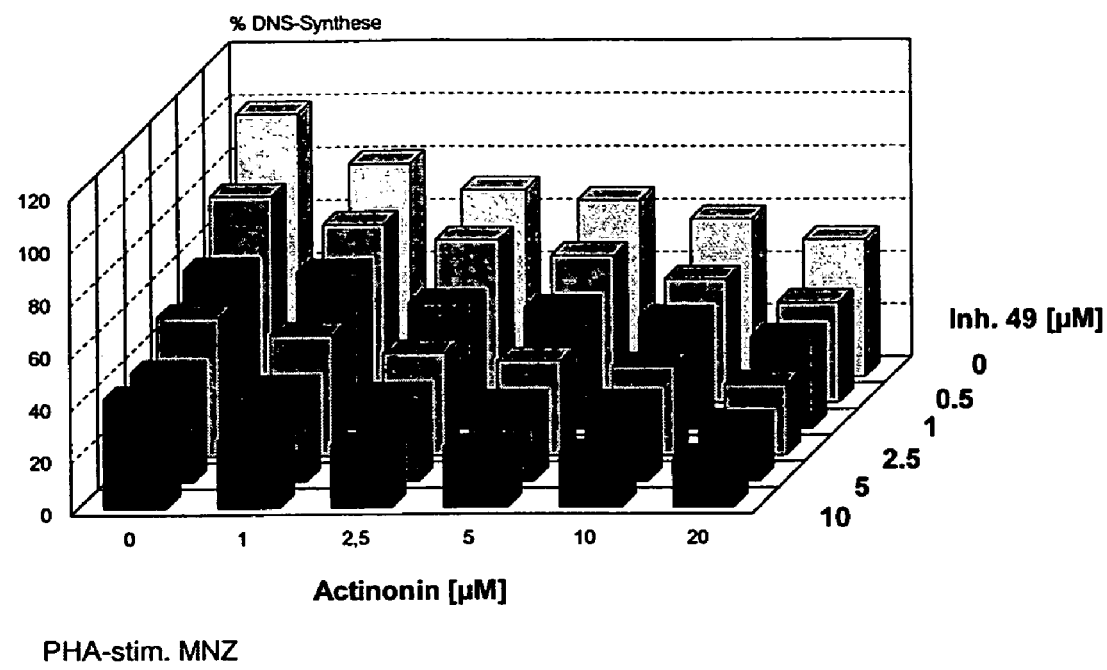

Our experiments showed that the DNA synthesis of human peripheric mononuclear cells (MNZ) is inhibited in a superadditive manner by a simultaneous administration of inhibitors of DP IV (Lys[Z(NO$_2$)]-thiazolidid=I49) and of APN (actinonine). The MNZ were incubated for 72 h in the presence of said inhibitors, and the DNA synthesis rate was determined subsequently by the measurement of the $^3$[H]-thymidine incorporation, as was described by Reinhold et al. [D. Reinhold et al.: "Inhibitors of dipeptidyl peptidase IV induce secretion of transforming growth factor β1 in PWM-stimulated PBMNC and T cells", Immunology 1997, 91, 354-360]. FIG. 2 shows the dose-dependent, superadditive inhibition of the DNA synthesis.

FIG. 2 shows the synergistic and dose-dependent effect of inhibitors of DP IV (I49) and APN (actinonine) on the DNA synthesis of human mononuclear cells (MNZ). Human MNZ were incubated for three days with the concentrations of inhibitors mentioned above. Subsequently, $^3$[H]-methyl thymidine was added to the culture medium, and the amount of $^3$[H]-thymidine incorporated into the DNA was measured after further 6 hours.

Example 3

Inhibition of the DNA Synthesis of Human T Lymphocytes by an Incubation with Synthetic Inhibitors of DP IV and of POP

Figure 3:
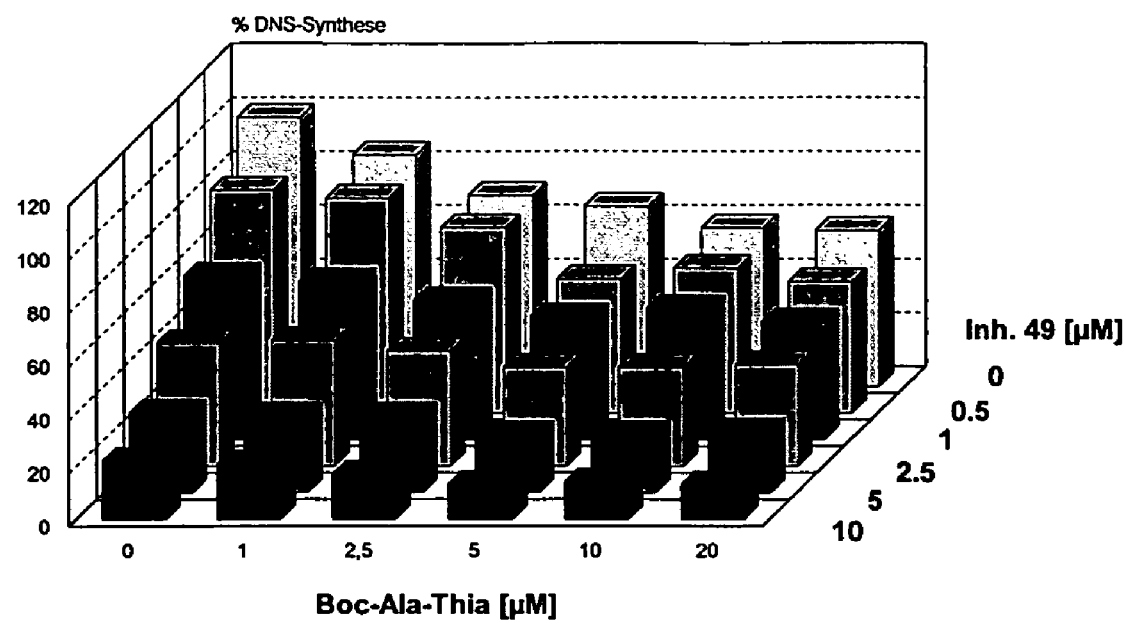

Our experiments showed that the DNA synthesis of human T lymphocytes is inhibited in a superadditive manner by a simultaneous administration of inhibitors of DP IV (Lys[Z(NO$_2$)]-thiazolidid=I49) and of prolyl oligopeptidase (Boc-Ala-thiazolidid). The T cells were incubated for 72 h in the presence of said inhibitors, and the DNA synthesis rate was determined subsequently by the measurement of the $^3$[H]-thymidine incorporation, as was described by Reinhold et al. [D. Reinhold et al.: "Inhibitors of dipeptidyl peptidase IV induce secretion of transforming growth factor β1 in PWM-stimulated PBMNC and T cells", Immunology 1997, 91, 354-360]. FIG. 3 shows the dose-dependent, superadditive inhibition of the DNA synthesis.

FIG. 3 show a the synergistic and dose-dependent effect of inhibitors of DP IV (I49) and of prolyl oligopeptidase (Boc-Ala-Thia) on the DNA synthesis of human peripheric T lymphocytes. Human T cells were incubated for three days with the concentrations of inhibitors mentioned above. Subsequently, $^3$[H]-methyl thymidine was added to the culture medium, and the amount of $^3$[H]-thymidine incorporated into the DNA was measured after further 6 hours.

Example 4

Inhibition of the DNA Synthesis of Human Peripheric Mononuclear Cells by an Incubation with Synthetic Inhibitors of DP IV and of POP

Figure 4:
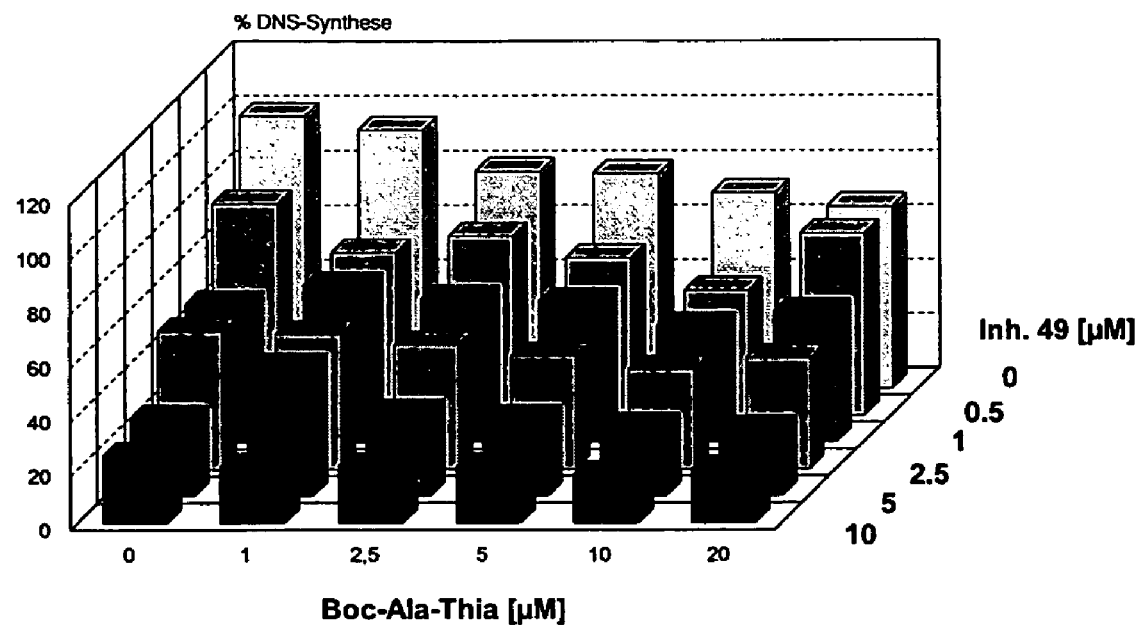

Our experiments showed that the DNA synthesis of human peripheric mononuclear cells (MNZ) is inhibited in a superadditive manner by a simultaneous administration of inhibitors of DP IV (Lys[Z(NO$_2$)]-thiazolidid=I49) and of prolyl oligopeptidase (Boc-Ala-Thiazolidid). The MNZ were incubated for 72 h in the presence of said inhibitors, and the DNA synthesis rate was determined subsequently by the measurement of the $^3$[H]-thymidine incorporation, as was described by Reinhold et al. [D. Reinhold et al.: "Inhibitors of dipeptidyl peptidase IV induce secretion of transforming growth factor β1 in PWM-stimulated PBMNC and T cells", Immunology 1997, 91, 354-360]. FIG. 4 shows the dose-dependent, superadditive inhibition of the DNA synthesis.

FIG. 4 shows the synergistic and dose-dependent effect of inhibitors of DP IV (I49) and of prolyl oligopeptidase (Boc-Ala-Thia) on the DNA synthesis of human mononuclear cells (MNZ). Human MNZ were incubated for three days with the concentrations of inhibitors mentioned above. Subsequently, $^3$[H]-methyl thymidine was added to the culture medium, and the amount of $^3$[H]-thymidine incorporated into the DNA was measured after further 6 hours.

Example 5

Inhibition of the DNA Synthesis of Human T Lymphocytes by an Incubation with Synthetic Inhibitors of DP IV and of ACE

Figure 5:
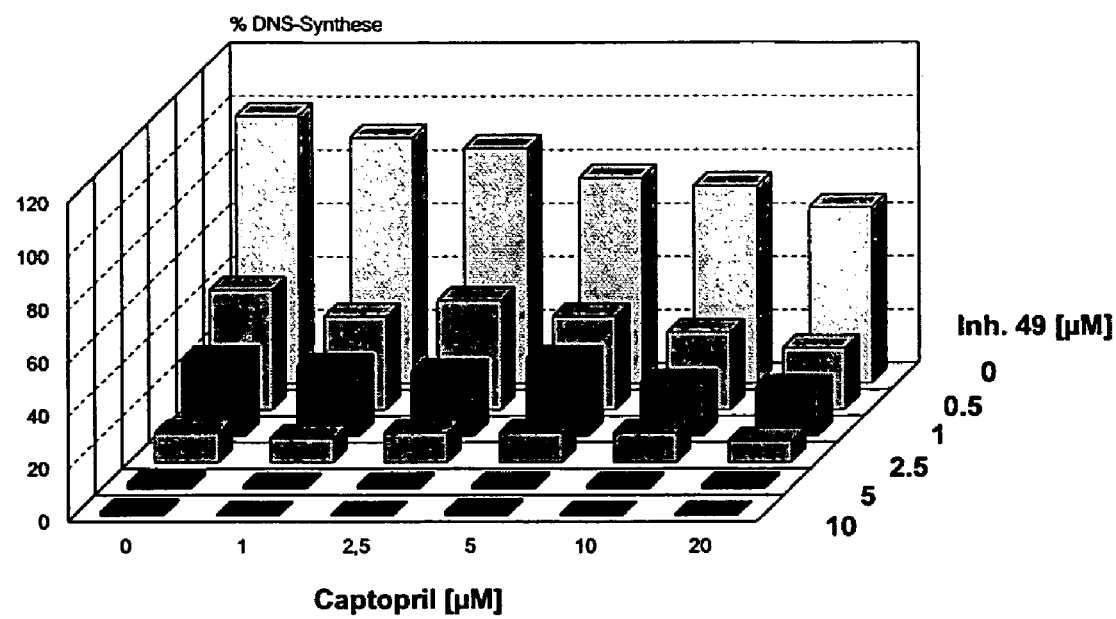

Our experiments showed that the DNA synthesis of human T lymphocytes is inhibited in a superadditive manner by a simultaneous administration of inhibitors of DP IV (Lys[Z(NO$_2$)]-thiazolidid=I49) and of the angiotensin-converting enzyme (Captopril). The T cells were incubated for 72 h in the presence of said inhibitors, and the DNA synthesis rate was determined subsequently by the measurement of the $^3$[H]-thymidine incorporation, as was described by Reinhold et al. [D. Reinhold et al.: "Inhibitors of dipeptidyl peptidase IV induce secretion of transforming growth factor β1 in PWM-stimulated PBMNC and T cells", Immunology 1997, 91, 354-360]. FIG. 5 shows the dose-dependent, superadditive inhibition of the DNA synthesis.

FIG. 5 shows the synergistic and dose-dependent effect of inhibitors of DP IV (I49) and of the angiotensin-converting enzyme (Captopril) on the DNA synthesis of human peripheric T lymphocytes. Human T cells were incubated for three days with the concentrations of inhibitors mentioned above. Subsequently, $^3$[H]-methyl thymidine was added to the culture medium, and the amount of $^3$[H]-thymidine incorporated into the DNA was measured after further 6 hours.

Example 6

Figure 6:
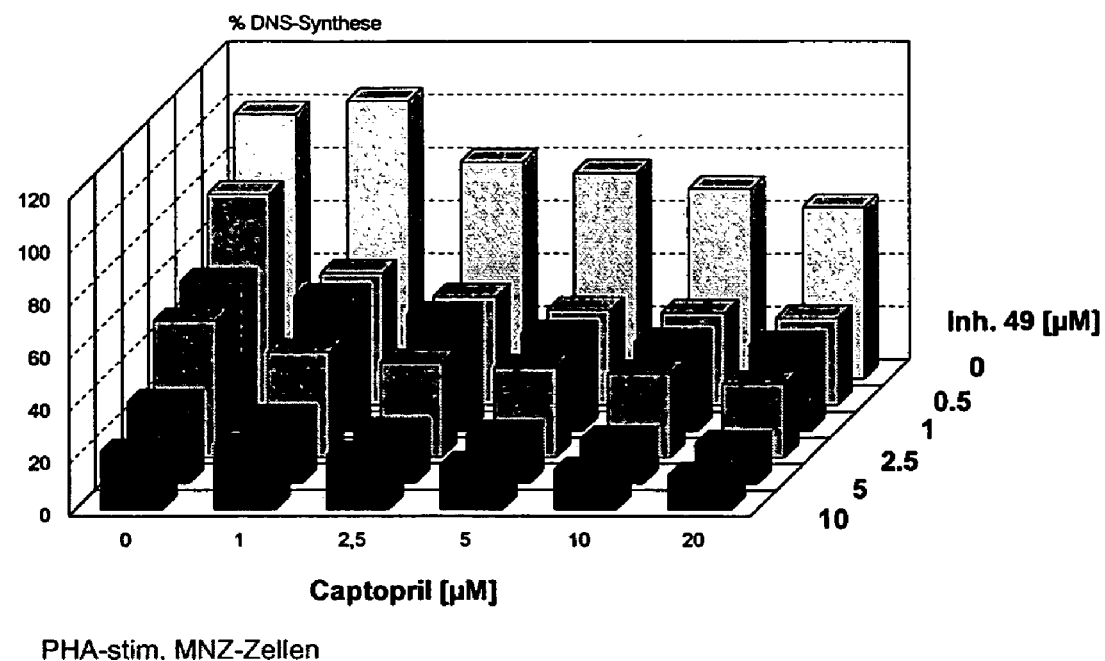

Inhibition of the DNA Synthesis of Human Peripheric Mononuclear Cells by an Incubation with Synthetic Inhibitors of DP IV and of ACE Our experiments showed that the DNA synthesis of human peripheric mononuclear cells (MNZ) is inhibited in a superadditive manner by a simultaneous administration of inhibitors of DP IV (Lys[Z(NO$_2$)]-thiazolidid=I49) and of the angiotensin-converting enzyme (Captopril). The MNZ were incubated for 72 h in the presence of said inhibitors, and the DNA synthesis rate was determined subsequently by the measurement of the $^3$[H]-thymidine incorporation, as was described by Reinhold et al. [D. Reinhold et al.: "Inhibitors of dipeptidyl peptidase IV induce secretion of transforming growth factor β1 in PWM-stimulated PBMNC and T cells", Immunology 1997, 91, 354-360]. FIG. 6 shows the dose-dependent, superadditive inhibition of the DNA synthesis.

FIG. 6 shows the synergistic and dose-dependent effect of inhibitors of DP IV (I49) and of the angiotensin-converting enzyme (Captopril) on the DNA synthesis of human mononuclear cells (MNZ). Human MNZ were incubated for three days with the concentrations of inhibitors mentioned above. Subsequently, $^3$[H]-methyl thymidine was added to the culture medium, and the amount of $^3$[H]-thymidine incorporated into the DNA was measured after further 6 hours.

Example 7

Inhibition of the Proliferation of Human Peripheric Mononuclear Cells (MNZ) by a Single and Simultaneous Administration of Inhibitory Substances of DP IV (I49=Lys[Z(NO$_2$)]-thiazolidid) and of APN (Actinonin)

Figure 7:
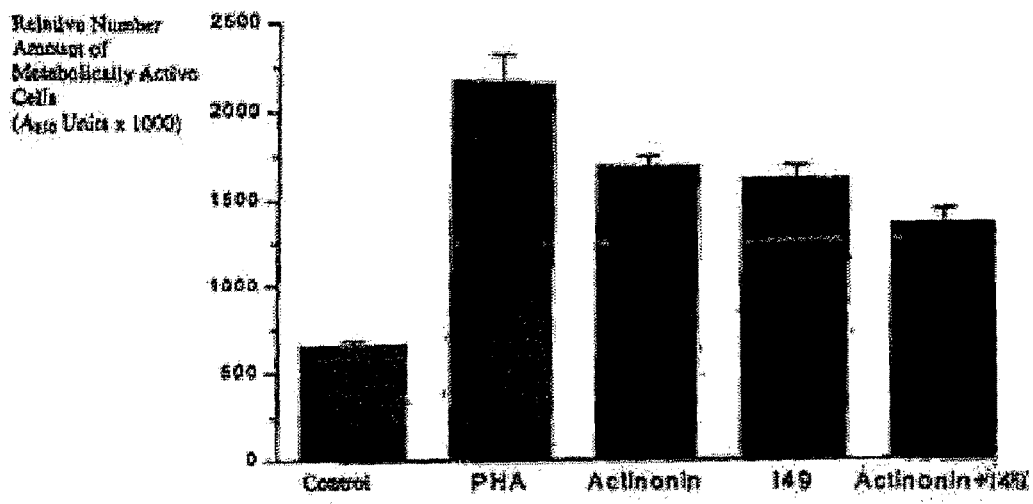

FIG. 7: The MNZ were incubated for a time period of 72 h without addition (control), with an addition of the mitogenic lectin phytohemagglutinin (PHA), and with the addition of PHA and the inhibitors mentioned above, respectively. Subsequently, the number amount of metabolically active cells was determined by using the commercially available WST-1 cell proliferation assay (Takara Inc.) in accordance with the provisions of the manufacturer.

Example 8

Inhibition of the Proliferation of the Human T Cell Line KARPAS-299 by a Single and Simultaneous Administration of Inhibitory Substances of DP IV (I49=Lys[Z(NO$_2$)]thiazolidid) and of APN (Actinonin and Probestin)

Figure 8:
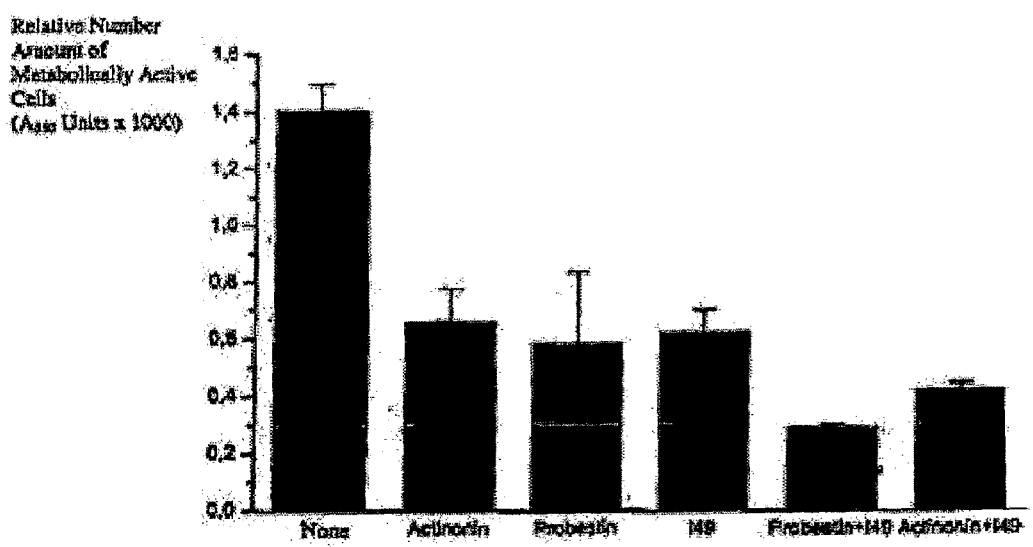

FIG. 8: The KARPAS-299 cells were incubated without addition (control) and in the presence of single inhibitors mentioned above as well as in the presence of combinations thereof, respectively. Subsequently, the number of metabolically active cells was determined by using the commercially available WST-1 cell proliferation assay (Takara Inc.) in accordance with the provisions of the manufacturer.

Example 9

Inhibition of the Proliferation of Activated Human Peripheric T Cells by a Single or Simultaneous Administration of Inhibitory Substances of DP IV (I49=Lys[Z(NO$_2$)]-thiazolidid) and of APN (Actinonin and Probestin)

Figure 9:
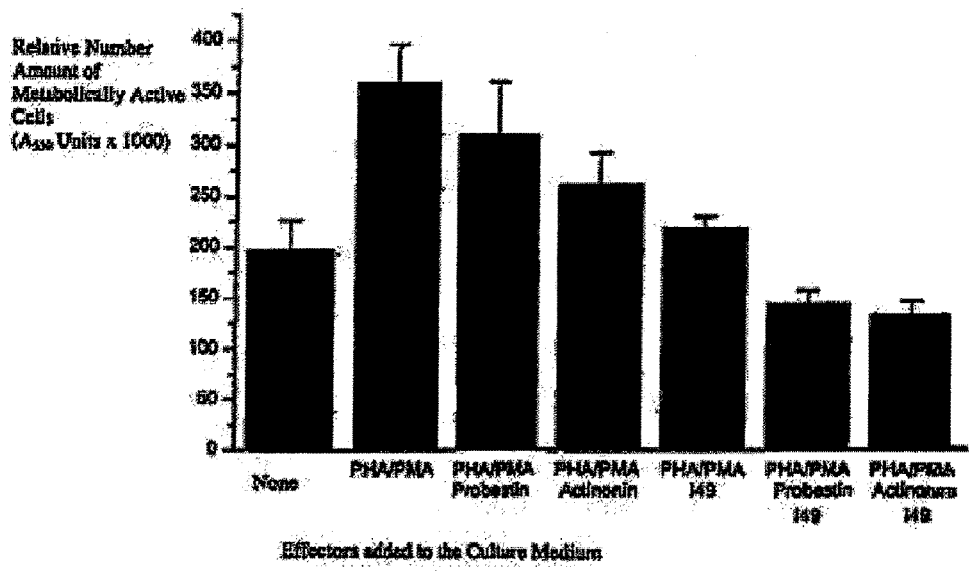

FIG. 9: The T cells, with the exception of the untreated control, were activated by an addition of phytohemagglutinine and phorbol-12-myristate-13-acetate to the culture medium and were incubated for a time period of 72 h in the presence of the above-mentioned inhibitors single and in combination. Subsequently, the number of metabolically active cells was determined by using the commercially available WST-1 cell proliferation assay (Takara Inc.) in accordance with the provisions of the manufacturer.

Example 10

Inhibition of the Proliferation of PHA-activated Human Mononuclear Cells (MNZ) by a Single or Simultaneous Administration of Inhibitory Substances of DP IV (I49=Lys[Z(NO$_2$)]thiazolidid) and of X-Pro-aminopeptidase (APP) (Apstatin)

Figure 10:
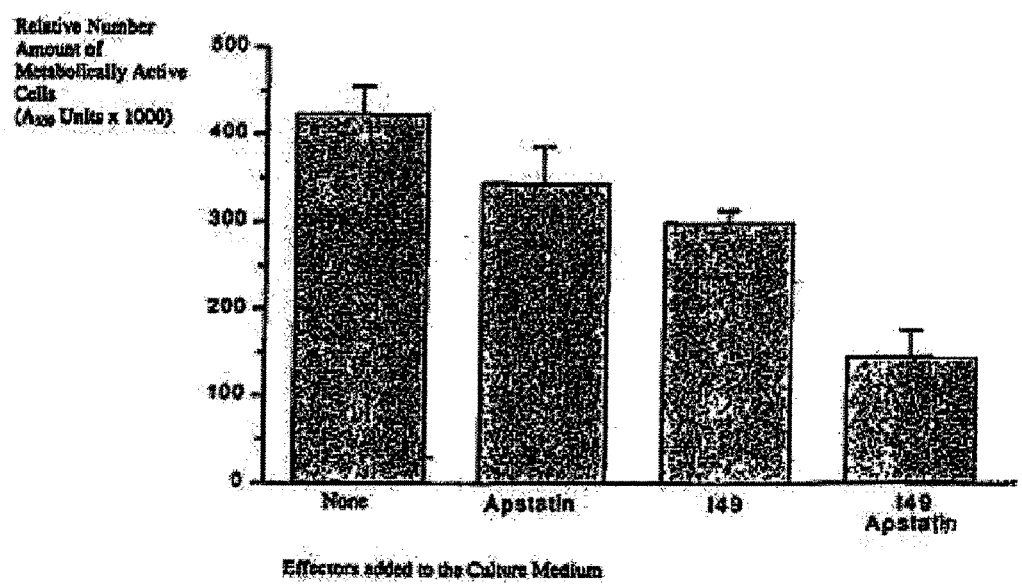

FIG. 10: The mononuclear cells (MNZ) were incubated for a time period of 72 h in the presence of the inhibitors mentioned above single and in combination. Subsequently, the number of metabolically active cells was determined by using the commercially available WST-1 cell proliferation assay (Takara Inc.) in accordance with the provisions of the manufacturer.

The invention claimed is:

1. Pharmaceutical preparation, comprising an inhibitor of dipeptidyl peptidase IV (DP IV) and of enzymes having DP IV-analogous enzyme activity, wherein the inhibitor of dipeptidyl peptidase IV (DP IV) and of enzymes having DP IV-analogous enzyme activity is Lys[Z(NO2)-thiazolidid,
   in combination with only one additional inhibitor, wherein the additional inhibitor is selected from the group of inhibitors consisting of actinonin, Boc-Ala-thiozolidid, captopril, probestin, and apstatin.

2. The pharmaceutical preparation of claim 1, wherein the additional inhibitor is actinonin.

3. The pharmaceutical preparation of claim 1, wherein the additional inhibitor is Boc-Ala-thiozolidid.

4. The pharmaceutical preparation of claim 1, wherein the additional inhibitor is captopril.

5. The pharmaceutical preparation of claim 1, wherein the additional inhibitor is probestin.

6. The pharmaceutical preparation of claim 1, wherein the additional inhibitor is apstatin.

7. The pharmaceutical preparation of claim 1, wherein the preparation further comprises a component selected from the group consisting of creams, ointments, pastes, gels, solutions, sprays, liposomes, shaked mixtures and hydrocolloid dressings.

* * * * *